(12) United States Patent
Kepert et al.

(10) Patent No.: US 6,372,932 B1
(45) Date of Patent: Apr. 16, 2002

(54) POROUS SOLID PRODUCTS OF 1,3, 5-BENZENETRICARBOXYLATE AND METAL IONS

(75) Inventors: Cameron J Kepert, Lilyfield (AU); Matthew J Rosseinsky, Wirral (GB)

(73) Assignee: University of Liverpool, Liverpool (GB)

( * ) Notice: Subject to any disclaimer, the term of this patent is extended or adjusted under 35 U.S.C. 154(b) by 0 days.

(21) Appl. No.: 09/463,818

(22) PCT Filed: Jul. 24, 1998

(86) PCT No.: PCT/GB98/02213

§ 371 Date: May 1, 2000

§ 102(e) Date: May 1, 2000

(87) PCT Pub. No.: WO99/05151

PCT Pub. Date: Feb. 4, 1999

(30) Foreign Application Priority Data

Jul. 25, 1997 (GB) ............................................. 9715825
Jan. 27, 1998 (GB) ............................................. 9801726

(51) Int. Cl.[7] ........................... C07F 15/04; C07F 15/06
(52) U.S. Cl. ........................ 556/147; 556/148; 556/150; 534/15
(58) Field of Search ............................. 556/147, 148, 556/150; 534/15

(56) References Cited

U.S. PATENT DOCUMENTS 5,648,508 A  7/1997  Yaghi ............................. 556/9

OTHER PUBLICATIONS

Kepert et al, "A porous chiral framework of coordinated . . . ," Chem. Commun., 00. 31–32 (1998).

Yaghi et al, "Construction of Porous Solids from Hydrogen-Bonded Metal . . . ," J. Am. Chem. Soc., vol. 118, pp. 9096–9101 (1996).

Yaghi et al, "Selective binding and removal of guestsin a microporous metal–organic framework," Nature (Letters to Nature), vol. 378, pp. 703–706 (1995).

*Primary Examiner*—Porfirio Nazario-Gonzalez
(74) *Attorney, Agent, or Firm*—Nixon & Vanderhye

(57) ABSTRACT

A solid product which is a porous chiral (10,3)-a network of 1,3,5-benzenetricarboxylate molecules of formula (I) where X is H, hydrocarbon, halide, etc, linked through metal atoms. Preferably the metal atoms are transition or lanthanide metal atoms carrying one or more coordinated ligands such as diols, preferably chiral ligands present in enantiomerically pure form

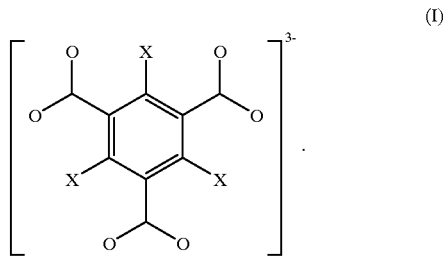

(I)

18 Claims, 9 Drawing Sheets

POROUS SOLID PRODUCTS OF 1,3,5-BENZENETRICARBOXYLATE AND METAL IONS

This invention relates to solid products which are both porous and chiral, by virtue of an absence of symmetry of a crystal structure of the atoms and molecules with its mirror image, involving reflection or inversion.

The search for porous chiral solids is driven largely by a desire to perform enantioselective separations and syntheses, processes which are of fundamental importance to the pharmaceuticals industry. Solid materials currently used to perform enantioseparations include natural and synthetic polymers, chiral sorbents and chiral membranes. Parallel with the search for solids is the synthesis of solution species for homogeneous catalysis and molecular recognition.

Yaghi O M et al (J Am. Chem. Soc. (1996) 118(38), 9096–9101; Nature (London) (1995), 378, (6558), 703–6; and U.S. Pat. No. 5,648,508) describe microporous materials which comprise for example chains or 2-dimensional nets of complexes of 1,3,5-benzenetricarboxylate with metal ions, said chains or nets being held together by hydrogen bonding or other specific interaction.

According to the present invention there is provided a porous chiral solid product which comprises two or more interpenetrating chiral (10, 3)-a networks of 1,3,5-benzenetricarboxylate molecules

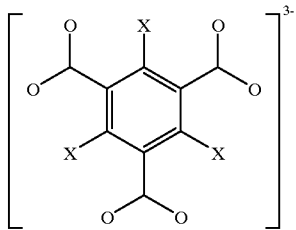

where X is H, hydrocarbon, halide, etc, linked through metal atoms. (10, 3)-a networks are structures containing 10-sided loops constructed with triangular connectors, as described by Wells. "Structural Inorganic Chemistry", $4^{th}$ Ed., Clarendon Press, Oxford, 1975 and "Three-Dimensional Nets and Polyhedra", Wiley-lnterscience, NY, 1977.

The solid product is an infinite molecular coordination network. The compounds described below are the only known infinite molecular coordination networks to be both chiral and porous, and are among only a handful of solids known to have both of these properties. These solid products contain three metal atoms for every two 1,3,5-benzenetricarboxylate molecules.

In the structural formula shown above, the groups X may be the same or different at different locations of the molecule. The nature of the group X is not specially critical. Preferably they are inert groups small enough not to cause steric hindrance such as lower ($C_1$–$C_5$) aliphatic groups or I, Br, Cl or F or particularly hydrogen atoms.

Preferably each metal atom acts as a linear connector between two 1,3,5-benzenetricarboxylate molecules. Preferably the metal is a transition or lanthanide metal having a coordination greater than 2. Preferably each metal atom (linking two 1,3,5-benzenetricarboxylate molecules) also carries one or more coordinated ligands. These ligands may be mono- or poly-dentate, and promising examples include alcohols, thiols, water, ammonia, aliphatic and aromatic amines and amides, halides, carboxylates, oxalate, nitrate, nitrite, sulfate, phosphate, oxide, sulfide, cyanide and thiocyanate. In desolvated salts (obtained by heating) it is not essential for all coordination sites of the metal atom to be satisfied by a coordinating ligand.

The metal atoms should preferably carry additional ligands that favour the linear coordination of the 1,3,5-benzenetricarboxylate and which satisfy the coordination environment of the metal. Although the binding of some ligands such as alcohols does in effect stabilise the structure by hydrogen-bonding, it is primarily the favourable energetics of formation of the structure, rather than the stability once it has formed that is important. Indeed, once formed, it is highly probable that heating the materials may liberate some of the bound ligands without destroying the framework structure.

When the metal has an oxidation state of 2, and these ligands are not electrically charged, then the solid product is electrically neutral. Alternatively if the metal atoms are in an oxidation state greater than or less than 2; and/or one or more of the ligands is electrically charged, then the whole molecular coordination network may be cationic or anionic. This may confer useful properties as described in more detail below.

The solid product may consist of four (10, 3)-a networks. Alternatively the solid product may consist of less than four such interpenetrating networks, and this may increase the solvent accessible volume of the product.

The solid product of the invention may be made by providing a solution of a metal salt, e.g. a transition or lanthanide metal salt, and a 1,3,5-benzenetricarboxylate as defined above, in a solvent consisting of one or more ligands for the chosen metal. Preferably the solution contains substantially three metal atoms for every two 1,3,5-benzenetricarboxylate molecules (btc). The desired product is recovered as a crystalline solid from the solution. Although each crystal is enantiomerically pure, the polycrystalline product may be a racemic mixture of crystals. While such a racemic mixture is useful for many of the purposes described below, it may be preferable to make an enantiomerically pure product, and this may be achieved either by using a chiral ligand for the metal, by forming the solid about a chiral template, by seeding crystal growth from a single enantiomeric crystal, by crystallising in the presence of a chiral cosolute, or by selective nucleation on a chiral surface.

The solid products of this invention have a number of features that make them promising for both chemical and physical application. Porous framework solids have several chemical uses, ranging from heterogeneous catalysis to molecular (neutral molecule, cation or anion) recognition and exchange. Forseeable chemical applications of the chiral (10, 3)-a network materials of btc include use (a) as catalysts that show stereo- and enantio-selectivity to reactants, products and transition-species, (b) as selective adsorbants, able to remove small components from reaction mixtures (and thereby influence reaction equilibria), to remove unwanted species from liquid or gaseous media (e.g. the removal of toxins from the environment), or to act as chromatographic phases for the separation of isomers and enantiomers, (c) as detectors in either the liquid or gaseous phase, (d) as hosts for reactive agents or biologically important molecules, enabling controlled release by diffusion, (e) as ion-exchange lattices.

The inclusion and physical manipulation of nanoparticle hosts in the cavities of porous solids opens up a range of physical applications, such as data storage and quantum electronics. Framework solids in many cases show unusual and useful mechanical properties, including structural hysteresis, negative coefficients of thermal expansion, and auxetic behaviour (negative Poisson's ratio). Finally, chiral solids find many applications which utilise their piezoelectric and optical rotatory properties.

Several porous chiral (10, 3)-a networks based on 1,3,5-benzenetricarboxylates have been characterised structurally. It is thought that a large and diverse family of materials with the same chiral framework structure may be synthesised. Notable differences between the structurally characterised materials support this claim: the structures form in different crystal systems (cubic and tetragonal), the coordination around the metal atom differs, the shapes of the pores differ considerably, and the solvent molecules occupying the cavities are different in each. The important and defining feature in the proposed family of salts is that a metal atom acts as a linear connector between two 1,3,5-benzenetricarboxylate anions, and that the planes of these anions are able to lie approximately orthogonal to each other (at 109.47° for a perfectly regular cubic (10, 3)-a network).

EXAMPLE 1

Five salts were characterised structurally, $[Ni^{II}(btc)_{2/3}(pyr)_2(eg)_2](eg)_x(H_2O)_y$ (A1), where x~1 and y~1.3;

$[Ni^{II}(btc)_{2/3}(pyr)_2(MeOH)_2](MeOH)_x(H_2O)_y$ (A2), where x~2 and y~1;

$[Ni^{II}(btc)_{2/3}(pyr)_2(EtOH)_2](EtOH)_x(H_2O)_y$ (A3), where x~1.5 and y~1;

$[Ni^{II}(btc)_{2/3}(pyr)_2(PrOH)](PrOH)_x(H_2O)_y$ (A4) where x~1.5 and y~1;

$[Co^{II}(btc)_{2/3}(pyr)_2(eg)](eg)_x(H_2O)_y$ (A5), where x~1 and y~1.3;

(where btc=1,3,5-benzenetricarboxylate, pyr=pyridine, eg=ethylene glycol, MeOH=methanol, EtOH=ethanol and PrOH=n-propanol). Four neutral (10, 3)-a networks interpenetrate, each related by translation or rotation (see FIGS. 1 to 4). Further materials have been synthesised by variation of the alcohol and metal units, and although these salts have yet to be characterised, their similar crystal morphologies suggest the novel framework structure is retained.

Crystallographic details of A1: cubic, space group $P4_232$, unit cell a=15.922(1) Å, V=4036.4(4) Å$^3$.

Crystallographic details of A2: tetragonal, space groups $P4_122$ and $P4_322$ (enantiomorphic pair), unit cell a=16.292(1) Å, c=29.139(1) Å, V=7734.3(7) Å$^3$.

Crystallographic details of A3: tetragonal, space groups $P4_122$ and $P4_322$, unit cell a=16.282(5) Å, c=30.911(8) Å, V=8195(4) Å$^3$.

Crystallographic details of A4: tetragonal, space group $P4_122/P4_322$, unit cell a=16.288(4) Å, c=30.811(10) Å, V=8174Å$^3$.

Crystallographic details of A5: cubic, space group $P4_232$, unit cell a=16.009(5) Å, V=4115 Å$^3$.

FIG. 1 shows part of the structure of compound (A). A nickel atom 10 acts as a linear connector between two btc molecules 12, 14. Other coordination positions of the nickel atom are occupied by two molecules of pyridine 16 and two molecules of ethylene glycol 18. It is believed that the whole structure may be stabilised by hydrogen bonds 20 formed between an oxygen atom of a btc molecule and an oxygen atom of ethylene glycol.

FIG. 2 shows a (10, 3)-a network structure involving btc molecules 12,14 connected by nickel atoms 10.

FIGS. 3(a) and 3(b) show the two enantiomers of the (10,3)-a network structure of FIG. 2.

FIG. 4 is a corresponding view of a solid product of the invention consisting of four interpenetrating networks of the kind shown in FIG. 3A or FIG. 3B.

For A1, A2, A3, A4 and A5, the solvent accessible volume between the four interpenetrating (10,3)-a networks is ca. 25% of the crystal volume (calculated using van der Waals radii). From the structure determination of the five different solvates it is evident that the network structure is robust enough to be insensitive to the nature of the solvent guests.

EXAMPLE 2

A new structural form of a porous chiral solid has been discovered, in which two distorted (10,3)-a networks interpenetrate. The networks are constructed by a 2:3 mixture of 1,3,5-benzenetricarboxylate anions and metal ions, such that the two of the former coordinates approximately linearly through one of the latter, and each of the carboxylate groups binds to a metal.

Six salts were characterised structurally, $[Ni^{II}(btc)_{2/3}(pyr)_2(pd)](pd)_x(H_2O)_y$ (B1) where x~3 and y~0;

$[Ni^{II}(btc)_{2/3}(pyr)_2(bd)](bd)_x(H_2O)_y$ (B2) where x~2.5 and y~0;

$[Ni^{II}(btc)_{2/3}(py)_2(12\text{-}bd)](12\text{-}bd)_x(H_2O)_y$ (B3) where x~2.5 and y~0;

$[Ni^{II}(btc)_{2/3}(py)_2(pentd)](pentd)_x(H_2O)_y$ (B4) where x~2.5 and y~0;

$[Ni^{II}(btc)_{2/3}(py)_2(bt)](bt)_x(H_2O)_y$ (B5) where x~2.5 and y~0;

$[Ni^{II}(btc)_{2/3}(py)_2(clpd)](clpd)_x(H_2O)_y$ (B6) where x~2.5 and y~0;

(where btc=1,3,5-benzenetricarboxylate, pyr=pyridine, pd=1,2-propanediol, bd=2,3-butanediol, 12-bd=1,2-butanediol, pentd=1,2-pentanediol, bt=1,2,4-butanetriol and clpd=3-chloro-1,2-propanediol).

Two neutral (10,3)-a networks interpenetrate (see FIGS. 5 to 8). The (10,3)-a networks are topologically the same as those seen in materials A1, A2, A3, A4 and A5 (Example 1), although here the networks are distorted due to the coordinated nickel atoms lying out of the plane of the anion's benzene plane. This solid contains only two (rather than four) interpenetrating (10,3)-a networks. As a result, the material has quite a different cavity structure to A1–A5, even though it is similar in many ways to the other salts: two btc anions are connected linearly through a $Ni^{II}$ cation, and the axial coordination sites of the metal are occupied by pyridine and alcohol (in the case of FIGS. 5–8, 1,2-propanediol) ligands. Importantly, the chirality of the framework material is coupled to the chirality of the alcohol that is coordinated to the metal (as determined by single crystal X-ray diffractometry). Enantiomerically pure (homochiral) samples of B may therefore be synthesised by using optically resolved diols.

Crystallographic details of B1: cubic, space group/$4_132$, unit cell a=28.471(1) Å, V=23078.5(14) Å$^3$.

Crystallographic details of B2: cubic, space group/$4_132$, unit cell a=28.457(1) Å, V=23045 Å$^3$.

Crystallographic details of B3: cubic, space group/$4_132$, unit cell a=28.988(2) Å, V=24359 Å$^3$.

Crystallographic details of B4: cubic, space group/$4_132$, unit cell a=28.970(4) Å, V=24313 Å$^3$.

Crystallographic details of B5: cubic, space group/$4_132$, unit cell a=29.5(3) Å, V=25700 Å$^3$.

Crystallographic details of B6: cubic, space group/$4_132$, unit cell a=28.970(2) Å, V=24313 Å$^3$.

FIG. 5 shows part of the structure of compound B1. A nickel atom 10 acts as a linear connector between two btc molecules 12, 14. Other coordination positions of the nickel atom are occupied by two molecules of pyridine 16 and one molecule of the bidentate (doubly coordinating) 1,2-propanediol molecule 18. It is believed that the whole structure is stabilised by hydrogen bonds 20 formed between oxygen atoms of the btc anion and alcoholic hydrogen atoms of the 1,2-propanediol.

Figure 1:
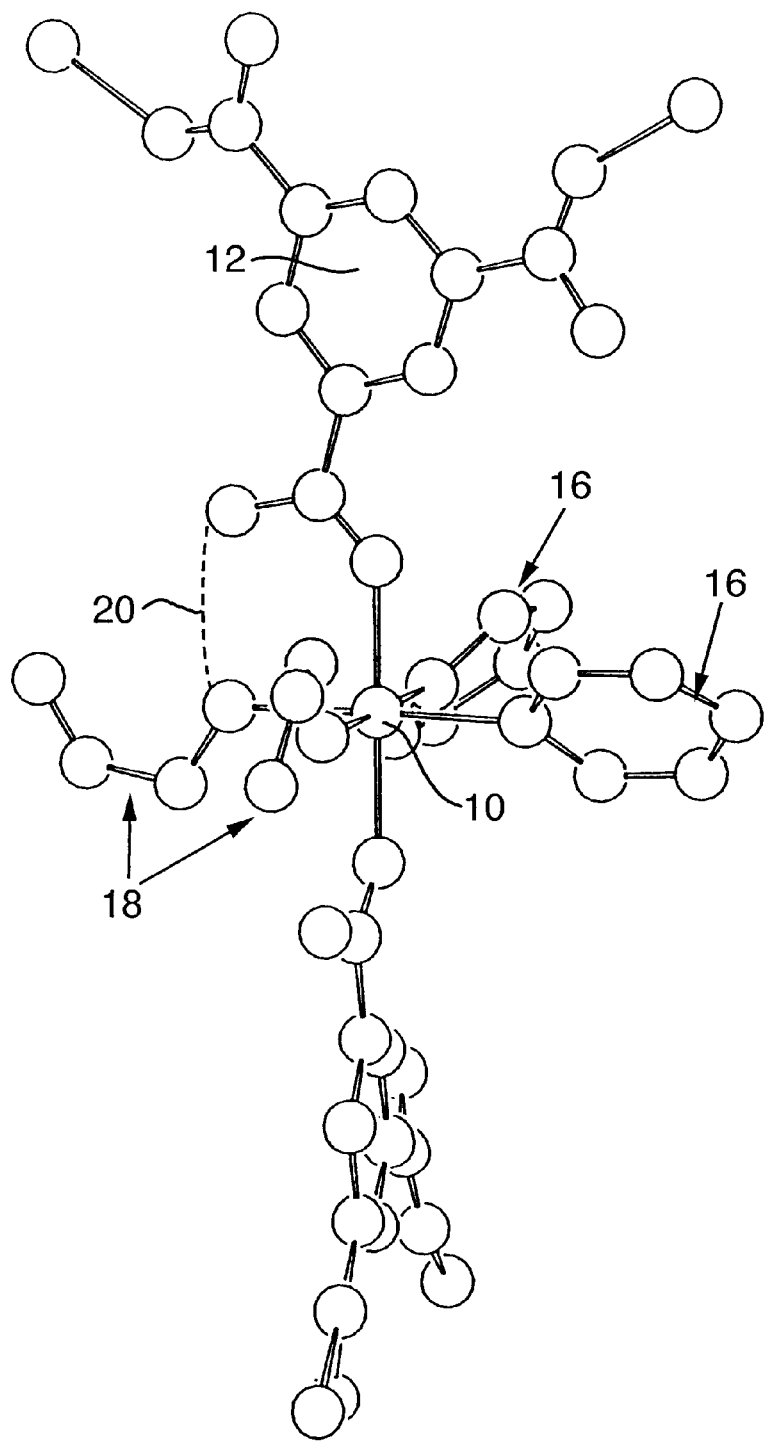
Figure 2:
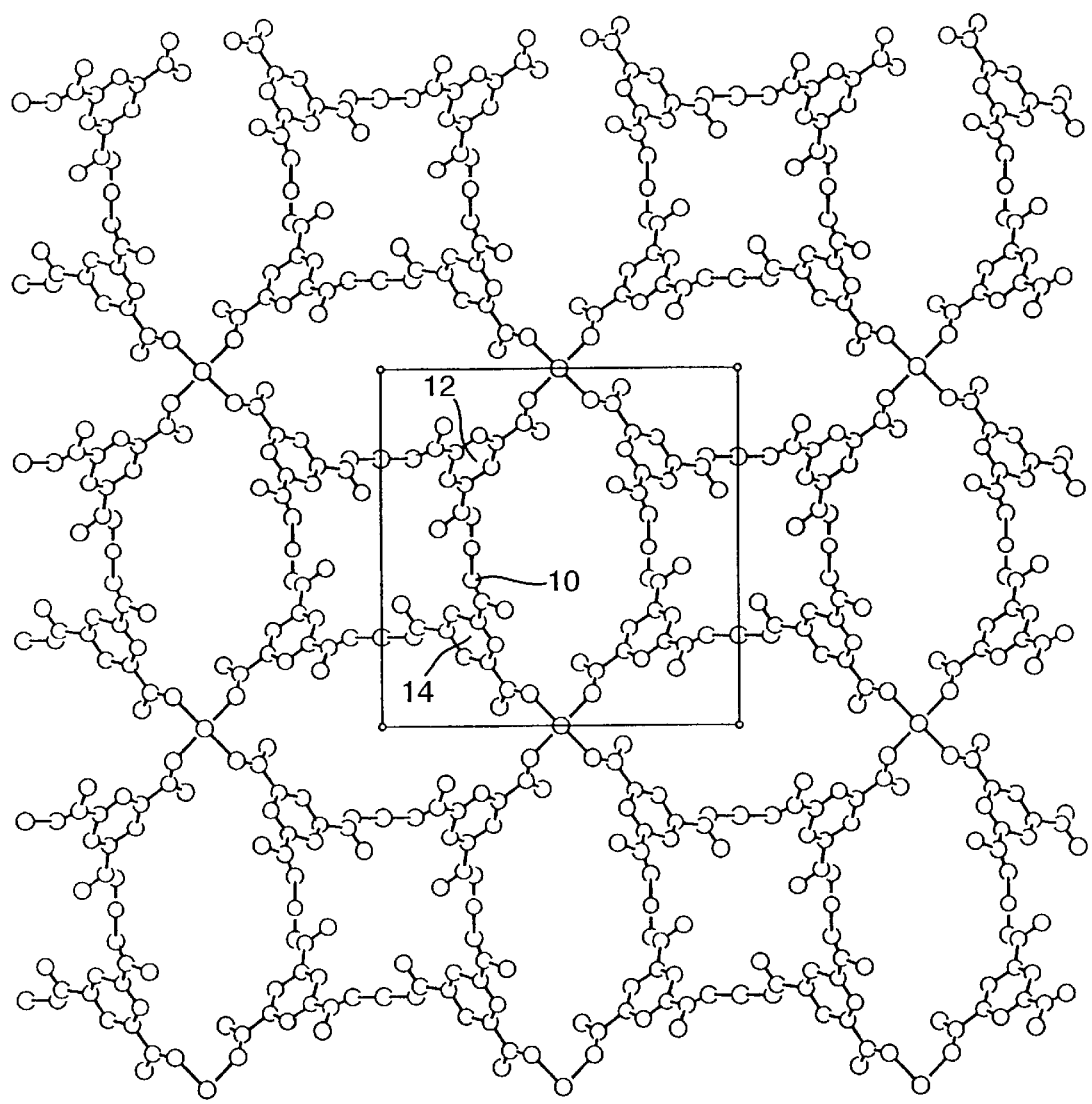
Figure 3A:
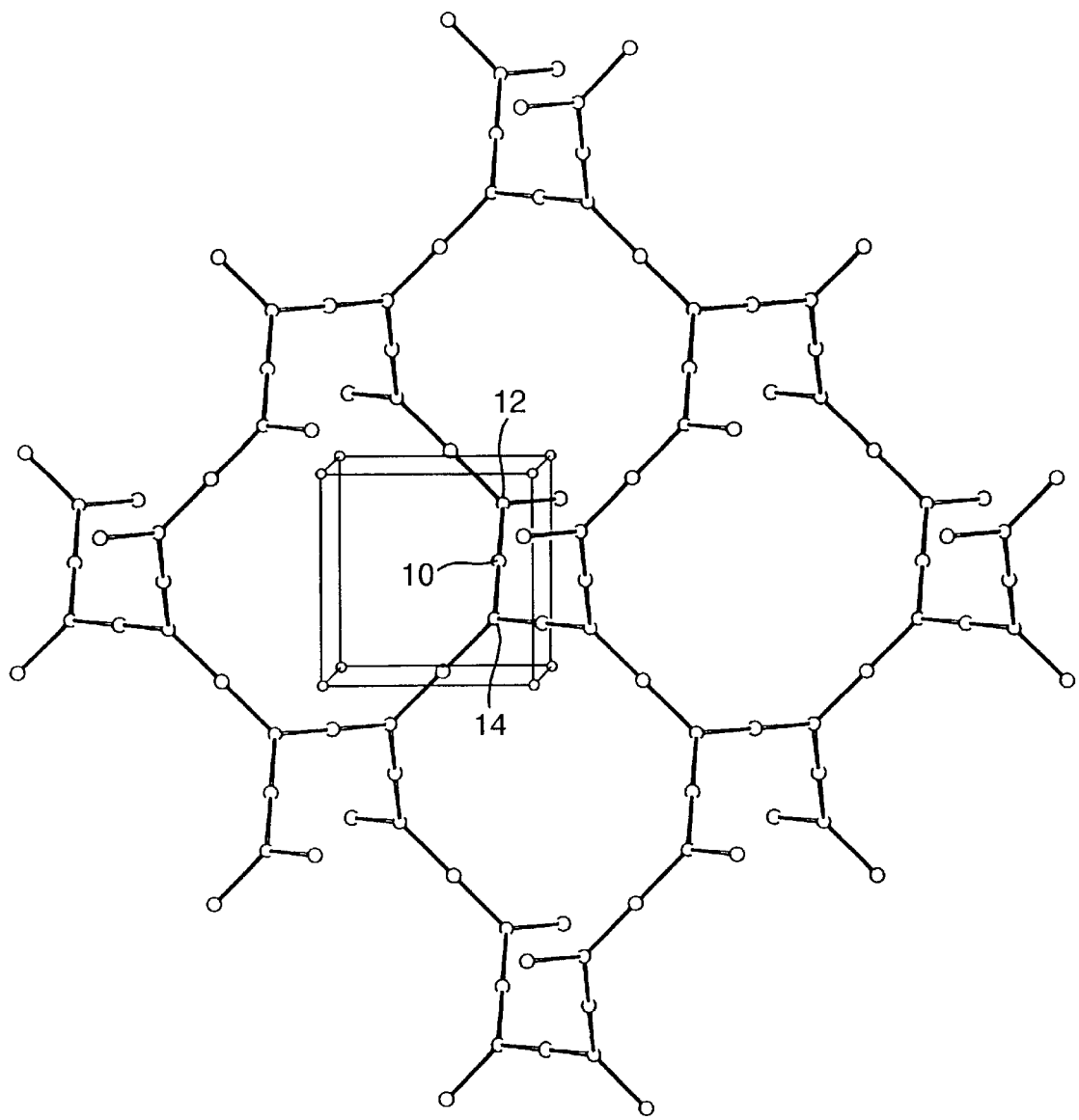
Figure 3B:
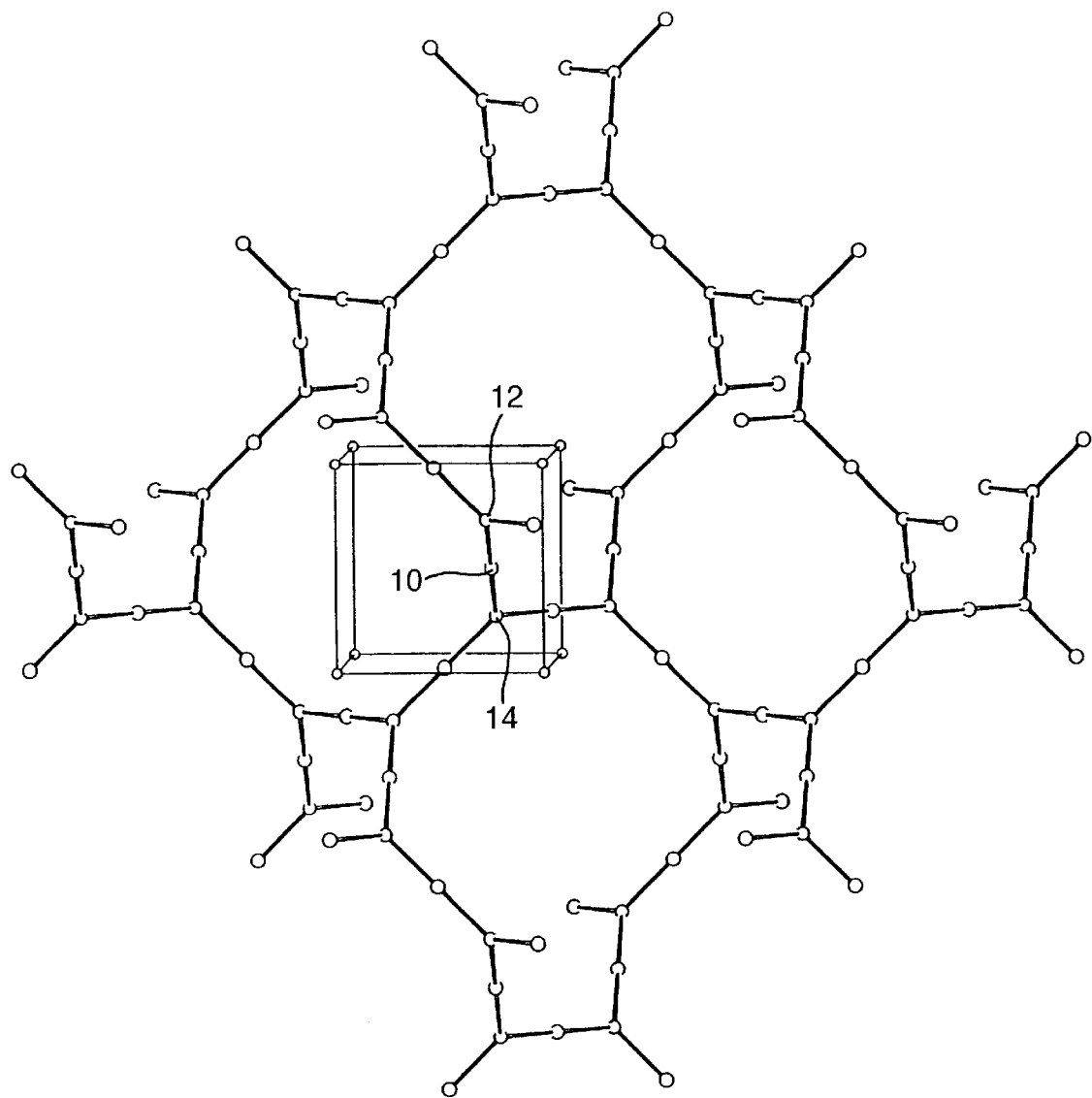
Figure 4:
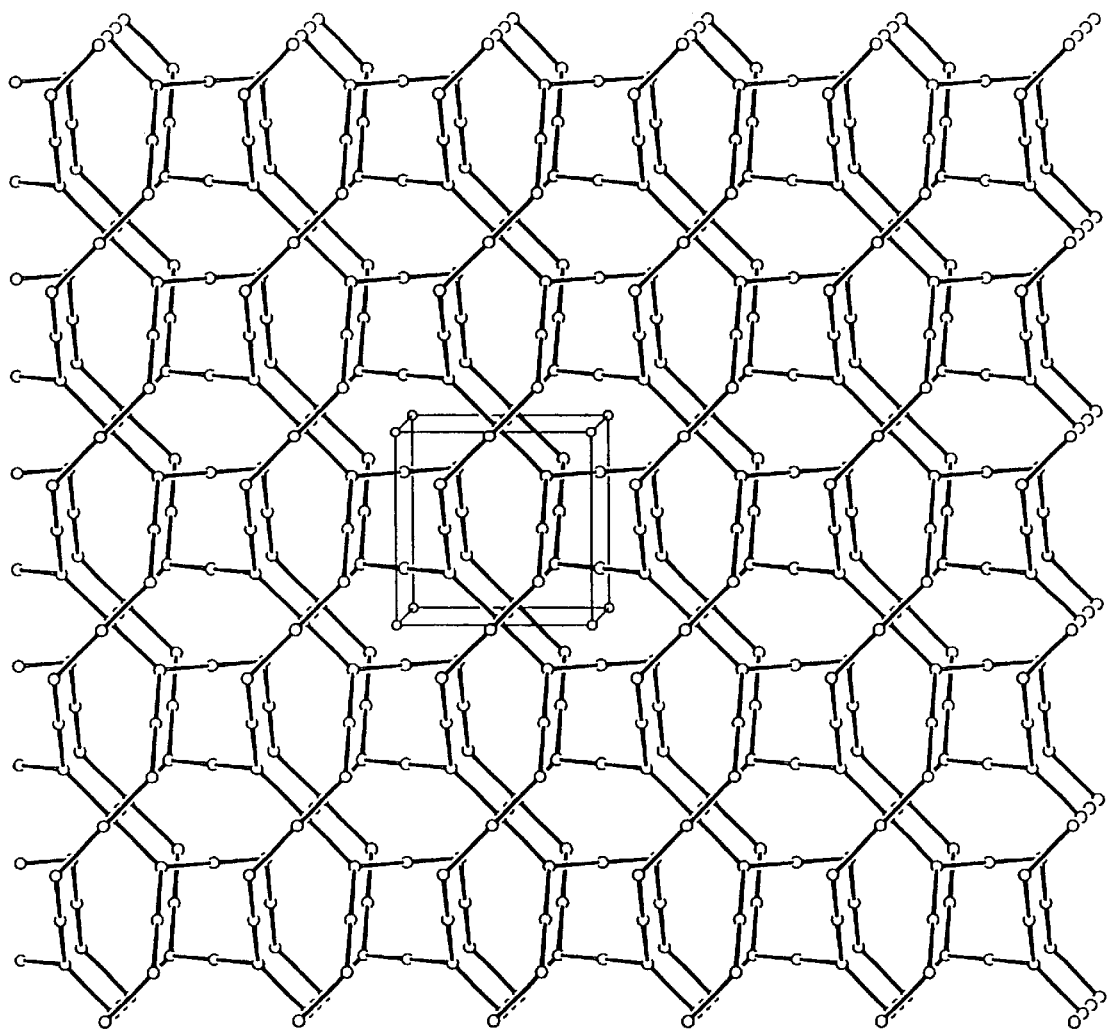
Figure 5:
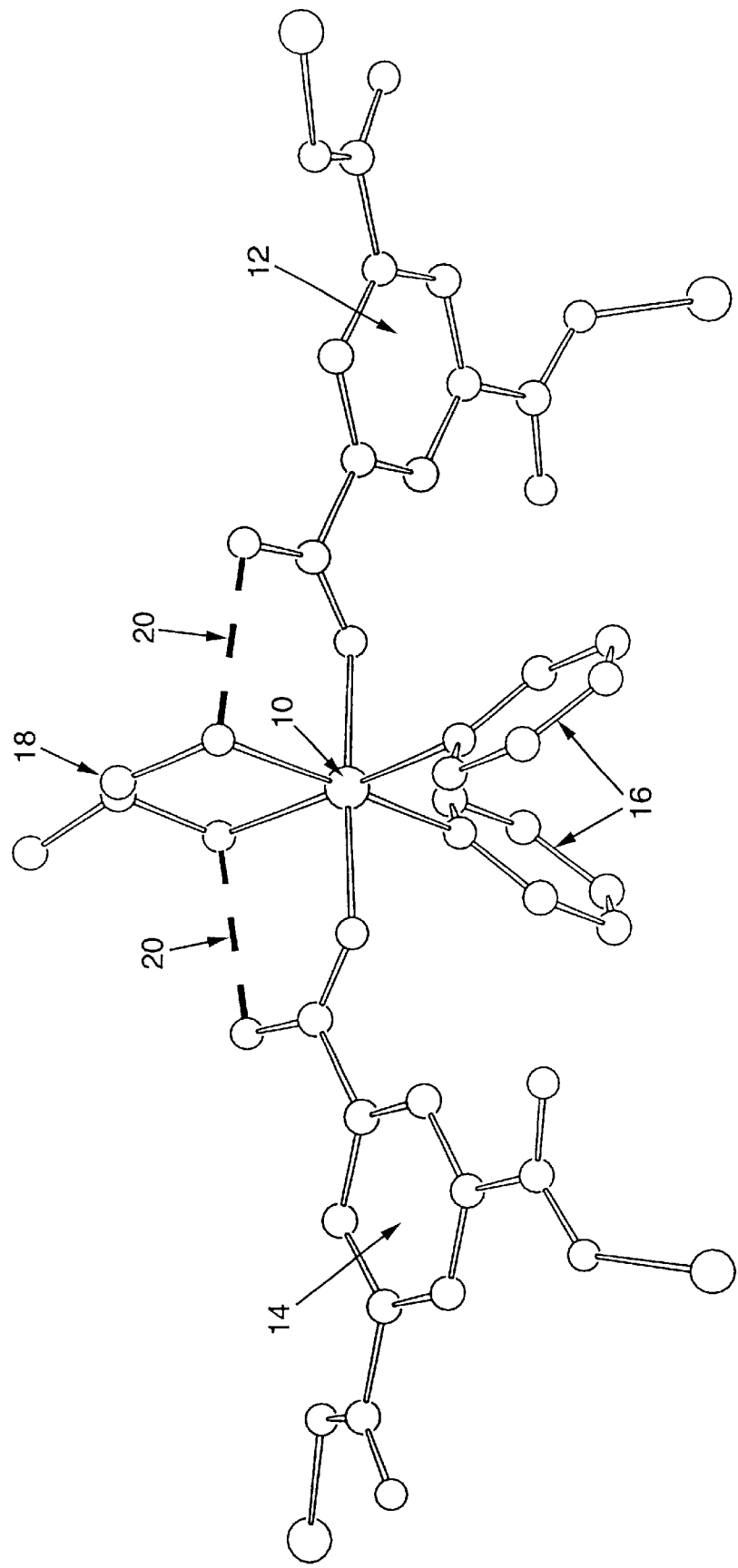
Figure 6:
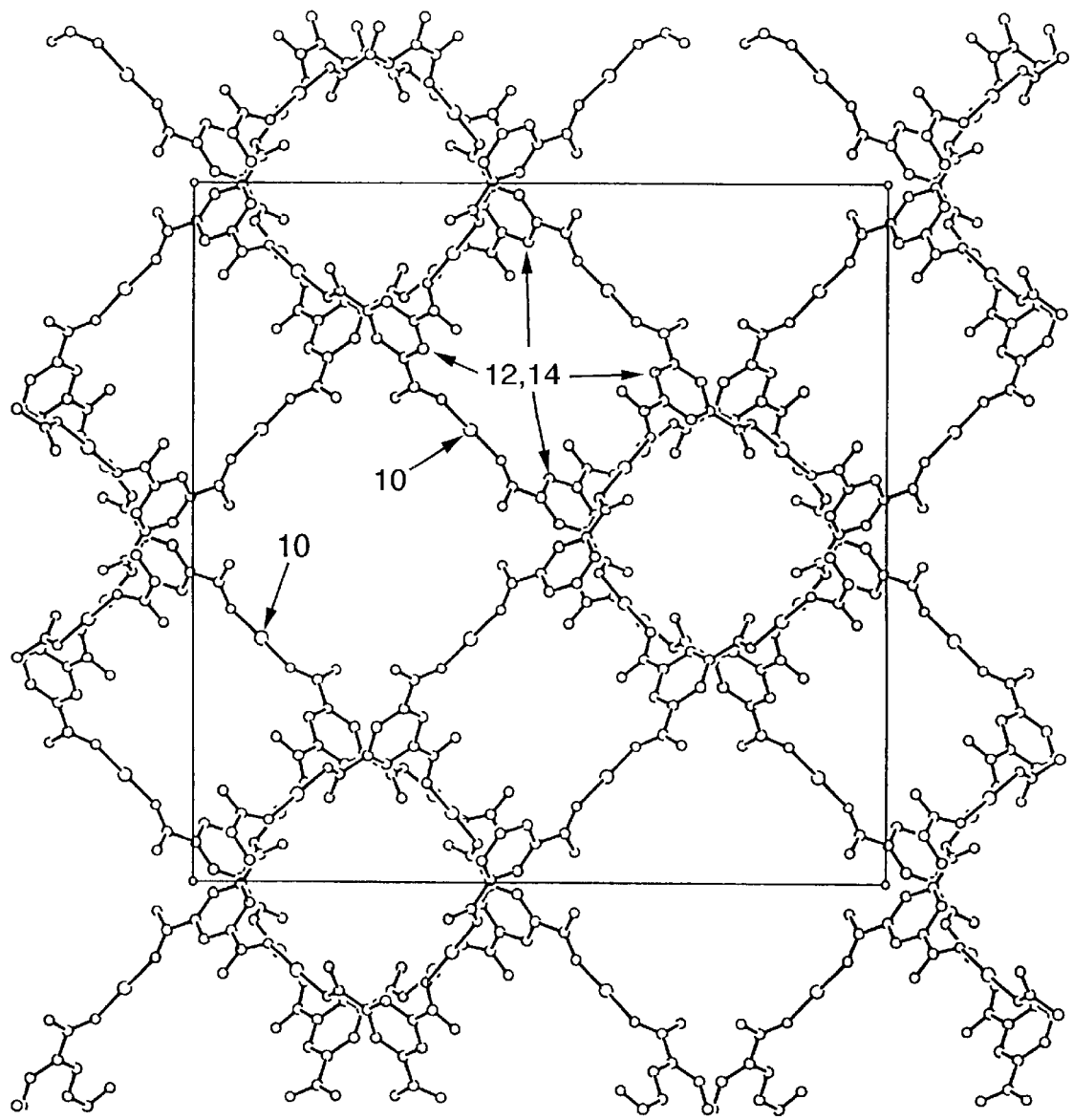
FIG. 6 shows a doubly-interpenetrating (10,3)-a network structure involving btc molecules 12, 14 connected by nickel atoms 10. The terminal ligands of the metal centres are omitted for clarity.
Figure 7:
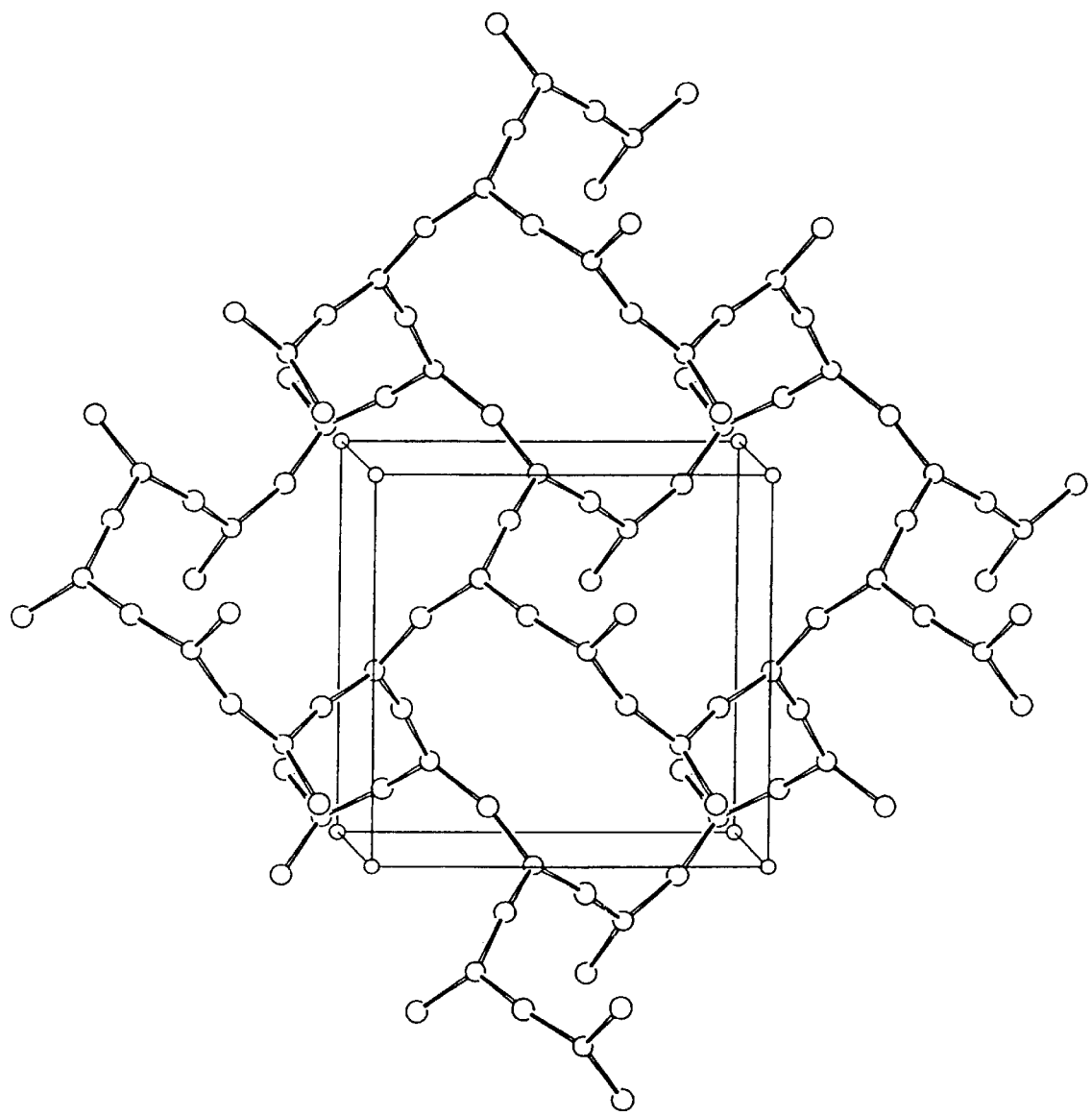
FIG. 7 shows a single distorted (10,3)-a network: linear connectors represent metal atoms and triangular connectors represent 1,3,5-benzenetricarboxylate anions.
Figure 8:
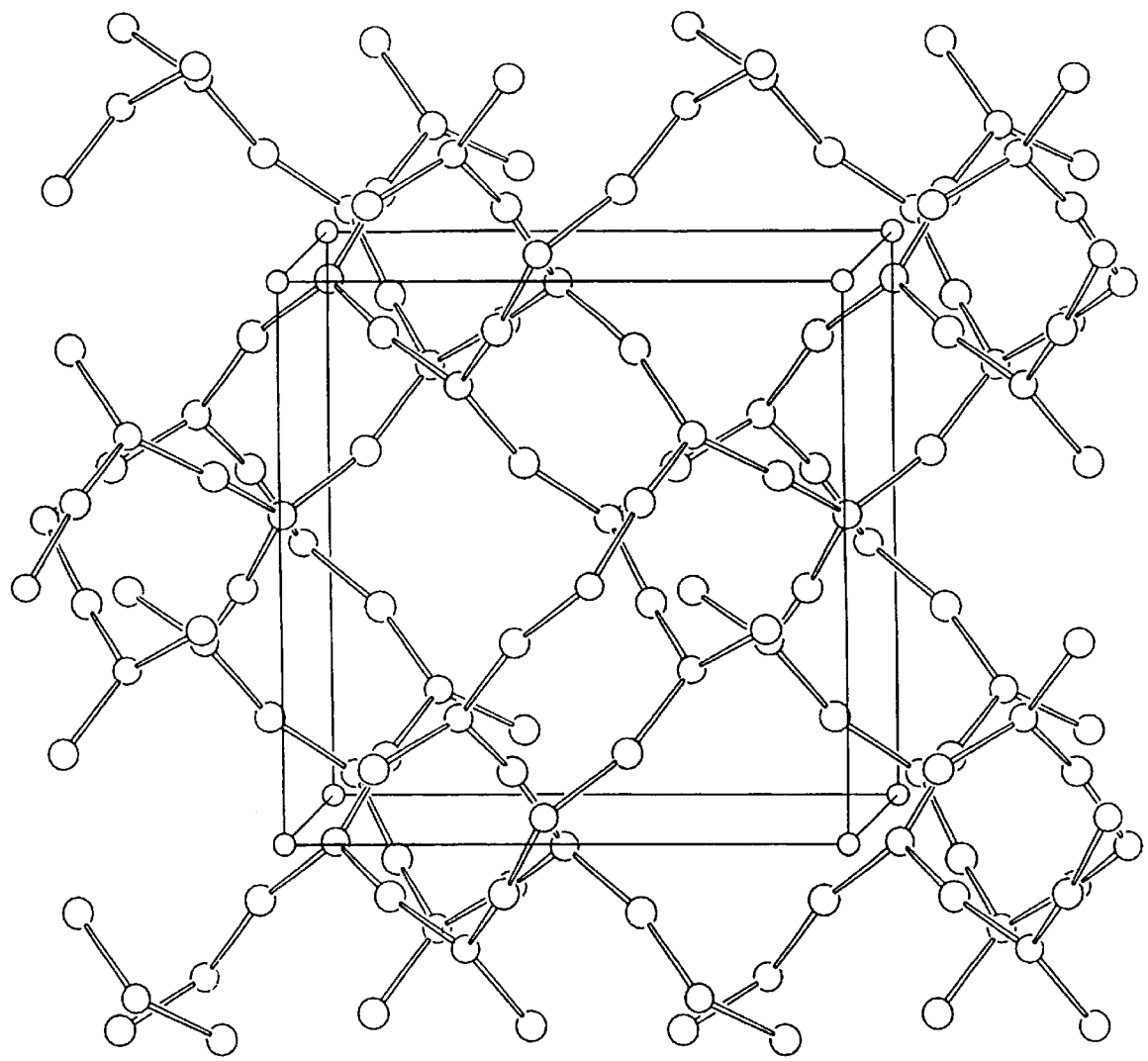
FIG. 8 is a conceptual view of a solid product of the invention consisting of two interpenetrating networks of the kind shown in FIG. 7.

For B1 and B2 the solvent accessible volume between the two interpenetrating (10,3)-a networks is ca. 50% of the crystal volume (calculated using van der Waals radii).

In all these materials, A1–A5 and B1–B6, the coordination around the metal centre is stabilised by hydrogen bonding between the hydrogen atom of the coordinated alcohol and the free oxygen atom of the carbonyl group of the anion. There is nothing unique about this arrangement, and a wide range of metal centres with a wide range of ligands may be envisaged, the only requirement being that this centre act as a linear connector for two 1,3,5-benzenetricarboxylate units. The solvent-filled cavities within the structure may therefore be varied systematically, the choice of ligands around the metal centre greatly influencing their chemical nature. With a potentially limitless number of arrays possible, it is expected that the cavities could be fine-tuned for very specific inclusion selectivities. Further important variations include (a) the formation of charged networks by altering the oxidation state of the metal or by changing the terminal coordinating ligands, thereby widening the applications of the framework to include cation and anion recognition, (b) the use of redox-active transition metal centres, promising to allow molecular recognition and catalysis via charge-transfer to the framework, (c) the synthesis of materials containing fewer than four interpenetrating (10, 3)-a networks by suitable choice of template molecules and reaction conditions, thereby greatly increasing the size of the cavities.

In the family of materials presented metal cations act as linear-connectors for the trigonal 1,3,5-benzenetricarboxylate anion. Most importantly, the distance between neighbouring btc units is too small to allow the interpenetration of networks of opposite chirality. Such a feature is seen, for example, in [Zn(tpt)$_{2/3}$(SiF$_6$)(H$_2$O)$_2$ (MeOH)] (tpt=2,4,6-tris(4-pyridyl)-1,3,5-triazine), which has eight interpenetrating networks, 4 of each handedness. In the structures presented, there are only two or four such networks, each with the same chirality. The relatively short molecular repeat distance of coordinated btc (ca. 10 Å) therefore dictates that (10, 3)-a network solids of this anion be chiral.

Solids of the (10,3)-a backbone may be synthesised enantiomerically pure by the coordination of a chiral ligand to the metal atom. Further methods of homochiral synthesis that offer great promise are selective nucleation at a chiral surface, seeding of crystal growth, use of a chiral molecular template, and crystallisation in the presence of a chiral cosolute. Separation of crystal according to their optical rotation may also become viable, since large transparent single crystals may be grown readily.

It is possible for solvent molecules in these infinite coordination complexes to be exchanged selectively without destroying crystallinity. In these molecular networks the inventors have shown that it is possible to desolvate single crystals whilst retaining monocrystallinity and porosity; and so as to retain the chiral network structure to give materials with large empty chiral cavities. These materials show selectivity to solvent reabsorption. Such materials may be expected to have many of the applications of zeolites, with additional advantages of the molecular solid state such as chemical diversity and crystallinity. Infinite coordination complexes therefore promise to become a highly important class of materials for heterogeneous catalysis and molecular recognition.

Example 1

Synthesis and Characterisation

Single crystals of A1, A2, A3 and A4 were grown by slow diffusion of pyridine into a stoichiometric 2:3 solution of trimesic acid (1,3,5-benzenetricarboxylic acid) and Ni(NO$_3$)$_2$.6H$_2$O in ethylene glycol (A1) or methanol (A2) or ethanol (A3) or n-propanol (A4). Single crystals of A5 were grown by slow diffusion of pyridine into a stoichiometric 2:3 solution of trimeric acid and Co(NO$_3$)$_2$.6H$_2$O in ethylene glycol. Many other salts have been synthesised by variation of the solvent or metal atom, and although these have yet to be structurally characterised, other methods of characterisation (see below) suggest these have the same quadruply-interpenetrating (10, 3)-a network structure. Diffusion techniques include the use of a) H-shaped cells, where the reactants diffuse toward one another through the horizontal arm of the vessel (useful when the solutions of the reactants are denser than the diffusion medium), b) test-tubes, where the reactants diffuse toward one another vertically (useful when the reactants are alternately more and less dense than the diffusion medium), c) non-aqueous gels based on tetramethoxysilane, where the species in solution diffuse towards one another in a U-tube or test-tube.

Large transparent single crystals (up to 2×2×2 mm) have been grown in H-cells over periods exceeding one month.

Structural Characterisation

Single crystals of A1 were placed in Lindemann capillaries and mounted both on an Enraf-Nonius DIP2000 diffractometer equipped with graphite-monochromated Mo—K$_\alpha$ radiation, a nitrogen gas cryostream and Eu/Ba image plate detectors, and on an Enraf-Nonius MACH3 diffractometer equipped with Cu—K$_\alpha$, radiation and a scintillation point detector. Structural refinement data were collected af 150 K with Mo—K$_\alpha$ and at 295 K with Cu—K$_\alpha$ radiation. On the MACH3 diffractometer a single quadrant of data was collected.

Single crystals of A2 were coated in an inert fluorinated oil, mounted on fine mohair fibres, and cooled either slowly or rapidly to 150 K on the DIP2000 diffractometer. For all crystals on the DIP2000 diffractometer 90 images were recorded, employing consecutive 2° oscillations in ω. The DIP2000 data were reduced with the HKL suite of programs. Structure solution was by a combination of Patterson and Fourier techniques using SHELXS-86 and SHELXL-93.

Powder samples of A3, A4 and A5, obtained by grinding a selection of single crystals, was placed in Lindemann capillaries and mounted on a Siemens D5000 powder X-ray diffractometer equipped with monochromated Cu—K$_\alpha$ radiation. Data were collected from 3 to 50° in 2θ. Peak indexing was achieved using the program DRAGON, and the unit cell parameters were refined using the program REFCEL.

Physical Characterisation

Raman spectra of single crystals of A1–A5 and some of the other salts synthesised have been collected on a DILOR LABRAM N°14/23IM red laser microscope spectrometer. The spectra show a large number of common features, suggesting all salts have the quadruply-interpenetrating (10,3)-network structure. The small differences between spectra are in all cases attributable to the variation of the alcohol solvent (which is present both in the cavities and coordinated to the metal atom).

Thermal gravimetric analyses of A1 and some of the other salts to be synthesised further suggest the existence of a large family of isomorphous materials. The temperature at which the materials liberate their cavity solvent molecules depends on the choice of solvent: ethylene glycol is liberated at ca. 110° C., ethanol at ca. 80° C., and methanol at room temperature (compound A2 is unstable in air).

Elemental Analysis

Elemental analysis of A1, A2 and A3 indicates their composition. Compound A1 is $Ni(btc)_{2/3}(pyr)_2(eg)_2.(eg)_x(H_2O)_y$, where $x\approx 1$ and $y\approx 1.3$, Compound A2 is $Ni(btc)_{2/3}(pyr)_2(MeOH)_2.(MeOH)_x(H_2O)_y$ where $x\approx 2$ and $y\approx 1$, and compound A3 (see below) is $Ni(btc)_{2/3}(pyr)_2(EtOH)_2.(EtOH)_x(H_2O)_y$ where $x\approx 1.5$ and $y\approx 1$. When these materials are heated to cause liberation of the solvent molecules in the cavities, there are obtained crystalline materials of the form $Ni(btc)_{2/3}(pyr)_x(alc)_y.(H_2O)_z$, where alc=eg, MeOH or EtOH, $x\approx 1.7$, $y\approx 1$ and $z\approx 1.3$. These desolvated materials may be resolvated by the vapours of a number of different solvents, thereby returning the materials to a highly crystalline state.

Example 2

Synthesis and Characterisation

Synthesis

Single crystals of B1, B2, B3, B4, B5 and B6 were grown by slow diffusion of pyridine into a stoichiometric 2:3 solution of trimesic acid (1,3,5-benzenetricarboxylate) and $Ni(NO_3)_2.6H_2O$ in either racemic or enantiomerically pure 1,2-propanediol (B1), 2,3-butanediol (B2), 12-bd=1,2-butanediol (B3), pentd=1,2-pentanediol (B4), bt=1,2,4-butanetriol (B5) and clpd=3-chloro-1,2-propanediol (B6); (to give either racemic or enantiomerically pure products, respectively). The diffusion techniques used were as in Example 1.

Structural Characterisation

Single crystals of B1 and B2 were coated in an inert fluorinated oil, mounted on fine mohair fibres, and cooled rapidly to 150 K on an Enraf-Nonius DIP2000 diffractometer. The diffractometer was equipped with graphite-monochromated Mo—$K_\alpha$ radiation, a nitrogen gas cryostream operating at 150 K, and Eu/Ba image plate detectors. Structural refinement data were collected at 150 K, reduced with the HKL suite of programs, and processed with the programs SHELXS-86 and SHELXL-93.

Powder samples of B3, B4, B5 and B6, obtained by grinding a selection of single crystals, was placed in Lindemann capillaries and mounted on a Siemens D5000 powder X-ray diffractometer equipped with monochromated Cu—$K_\alpha$ radiation. Data were collected from 3 to 50° in 2θ. Peak indexing was achieved using the program DRAGON, and the unit cell parameters were refined using the program REFCEL.

Physical Characterisation

Thermal gravimetric analyses of B1–B6 indicate that the solvent molecules are liberated from the cavities in the range 50° C. to 100° C.

What is claimed is:

1. A porous chiral solid product which comprises two to four interpenetrating chiral (10,3)-networks of 1,3,5-benzenetricarboxylate molecules

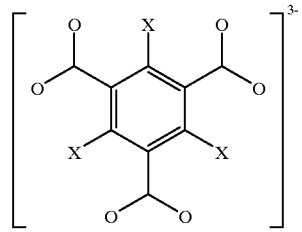

where X is H, hydrocarbon, or halide linked through metal atoms.

2. A solid product as claimed in claim 1, wherein the metal is a transition or lanthanide metal.

3. A solid product as claimed in claim 1, wherein each metal atom acts as a linear connector between two 1,3,5-benzenetricarboxylate molecules.

4. A solid product as claimed in claim 1, wherein each metal atom carries one or more coordinated ligands selected alcohols, thiols, water, ammonia, aliphatic and aromatic amines and amides, halides, carboxylates, oxalate, nitrate, nitrite, sulfate, phosphate, oxide, sulfide, cyanide and thiocyanate.

5. A solid product as claimed in claim 4, wherein the ligand is a chiral ligand present in enantiomerically pure form.

6. A solid product as claimed in claim 4, wherein the ligand is a diol.

7. A solid product as claimed in claim 1, which is enantiomerically pure.

8. A solid product as claimed in claim 1, wherein four interpenetrating chiral (10,3)-a networks are present.

9. A solid product as claimed in claim 1, wherein two interpenetrating chiral 910,3)-a networks are present.

10. A solid product as claimed in claim 1, which is $[Ni^{II}(btc)_{2/3}(pyr)_2(eg)_2](eg)_x(H_2O)_y$ where x is about 1 and y is about 1.3, or $[Ni^{II}(btc)_{2/3}(pyr)_2(MeOH)_2](MeOH)_x(H_2O)_y$ where x is about 2 and y is about 1, or $[Ni^{II}(btc)_{2/3}(pyr)_2(EtOH)_2](EtOH)_x(H_2O)_y$ where x is about 1.5 and y is about 1, or $[Ni^{II}(btc)_{2/3}(pyr)_2(PrOH)](PrOH)_x(H_2O)_y$ where x is about 1.5 and y is about 1, or $[Co^{II}(btc)_{2/3}(pyr)_2(eg)](eg)_x(H_2O)_y$ where x is about 1 and y is about 1.3, where btc is 1,3,5-benzenetricarboxylate, pyr is pyridine and eg is ethylene glycol.

11. A crystalline material as claimed in claim 9, which is $Ni^{II}(btc)_{2/3}(pyr)_x(diol)](diol)_x(H_2O)_y$ where x is about 2.5–3 and y is about 0.

12. A solid product as claimed in claim 11, wherein the diol is 1,2-propanediol, 2,3-butanediol, 1,2-butanediol, 1,2-pentanediol, 1,2,4-butanediol or 3-chlor-1,2-propanediol.

13. A crystalline material having chiral cavities that results from desolvation of the solid product of claim 4.

14. A crystalline material as claimed in claim 13 which is $Ni^{II}(btc)_{2/3}(pyr)_x(alc)_y(H_2O)_z$ where alc is MeOH or EtOH, x is about 1.7, y is about 1 and z is about 1.3.

15. A method of making the solid product of claim 1, which method comprises providing a solution of a transition or lanthanide metal salt and a 1,3,5-benzenetricarboxylate as defined in claim 1, containing substantially three metal atoms for every two 1,3,5-benzenetricarboxylate molecules, in one or more ligands selected from alcohols, thiols, water, ammonia, aliphatic and aromatic amines and amides, halides, carboxylates, oxalate, nitrate, nitrite, sulfate, phosphate, oxide, sulfide, cyanide and thiocyanate, and recovering the desired solid product from the solution.

16. A method as claimed in claim 15, wherein a chiral ligand in enantiomerically pure form is used in order to obtain a solid product in enantiomerically pure form.

17. A solid product as claimed in claim 1, wherein X is a lower ($C_1$–$C_5$) aliphatic group.

18. A solid product as claimed in claim 1, wherein said halide is selected from the group consisting of F, Cl, Br and I.

\* \* \* \* \*